(12) United States Patent
Mate et al.

(10) Patent No.: US 8,758,779 B2
(45) Date of Patent: Jun. 24, 2014

(54) PHARMACEUTICAL COMPOSITION OF DULOXETINE

(75) Inventors: Sanjay Mate, Pune (IN); Ritesh Kapoor, Mandi (IN); Inderjeetsingh Huda, Aurangabad (IN); Kasturi Roy, Uttarpara (IN); Munish Talwar, Panchkula (IN); Girish Kumar Jain, Delhi (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 121 days.

(21) Appl. No.: 13/377,968

(22) PCT Filed: Jun. 24, 2010

(86) PCT No.: PCT/IB2010/052879
§ 371 (c)(1),
(2), (4) Date: Mar. 17, 2012

(87) PCT Pub. No.: WO2010/150219
PCT Pub. Date: Dec. 29, 2010

(65) Prior Publication Data
US 2012/0164216 A1    Jun. 28, 2012

(30) Foreign Application Priority Data

Jun. 25, 2009 (IN) .......................... 1506/MUM/2009
Jun. 25, 2009 (IN) .......................... 1507/MUM/2009

(51) Int. Cl.
*A61K 9/28* (2006.01)
*A61K 9/16* (2006.01)
*A61K 9/14* (2006.01)
*A61K 31/381* (2006.01)
*A61K 9/00* (2006.01)

(52) U.S. Cl.
CPC ............. *A61K 31/381* (2013.01); *A61K 9/1652* (2013.01); *A61K 9/146* (2013.01); *A61K 9/1635* (2013.01); *A61K 9/0095* (2013.01)
USPC .......................... 424/400; 400/474; 400/483

(58) Field of Classification Search
None
See application file for complete search history.

(56) References Cited

U.S. PATENT DOCUMENTS

| | | | |
|---|---|---|---|
| 5,508,276 A * | 4/1996 | Anderson et al. ............. | 514/183 |
| 5,811,436 A | 9/1998 | Leonard et al. | |
| 6,132,771 A * | 10/2000 | Depui et al. .................. | 424/468 |
| 2006/0079569 A1 | 4/2006 | Sesha | |
| 2006/0182796 A1 | 8/2006 | Wu et al. | |
| 2008/0003296 A1 | 1/2008 | Ketner | |

FOREIGN PATENT DOCUMENTS

| | | | |
|---|---|---|---|
| EP | 0693282 A2 | | 1/1996 |
| WO | WO2007/034503 A2 | | 3/2007 |
| WO | WO 2007034503 A2 | * | 3/2007 |
| WO | WO 2008129501 A2 | * | 10/2008 |
| WO | WO2008129501 A2 | | 10/2008 |
| WO | WO2009084017 A2 | | 7/2009 |

* cited by examiner

*Primary Examiner* — Nissa Westerberg
(74) *Attorney, Agent, or Firm* — Bio Intellectual Property Services LLC (Bio IPS); O. (Sam) Zaghmout

(57) ABSTRACT

The invention relates to a taste masked pharmaceutical composition comprising duloxetine or pharmaceutically acceptable salts thereof. The invention also relates to processes for the preparation of such compositions. The invention further discloses an inclusion complex comprising duloxetine or pharmaceutically acceptable salts thereof with one or more cyclodextrin or derivatives thereof.

13 Claims, 1 Drawing Sheet

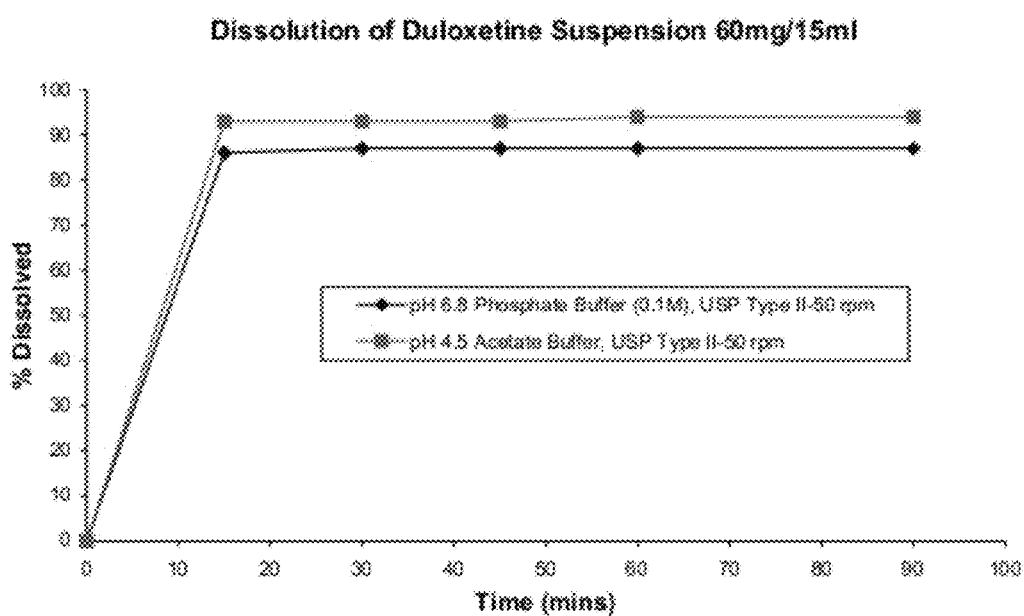

PHARMACEUTICAL COMPOSITION OF DULOXETINE

FIELD OF THE INVENTION

The invention relates to a taste masked pharmaceutical composition comprising duloxetine or pharmaceutically acceptable salts thereof. The invention also relates to processes for the preparation of such compositions. The invention further discloses an inclusion complex comprising duloxetine or pharmaceutically acceptable salts thereof with one or more cyclodextrin or derivatives thereof.

BACKGROUND OF THE INVENTION

Duloxetine is marketed as duloxetine Hydrochloride under the trade name Cymbalta® by Eli Lilly. Chemically Duloxetine hydrochloride is (+)-(S)—N-methyl-γ-(1-naphthyloxy) 2-thiophenepropylamine hydrochloride having structure of formula I. Cymbalta® is indicated for the acute and maintenance treatment of major depressive disorder, acute treatment of generalized anxiety disorder and for the management of neuropathic pain associated with diabetic peripheral neuropathy. It is also indicated for the management of fibromyalgia.

U.S. Pat. No. 5,023,269 discloses duloxetine and the pharmaceutically acceptable acid addition salts thereof.

U.S. Pat. No. 5,508,276 discloses formulation of duloxetine in the form of enteric pellets comprising hydroxypropylmethylcellulose acetate succinate.

U.S. Pat. No. 6,596,756 discloses a method of treating fibromyalgia by administering an effective amount of Duloxetine.

U.S. Patent Application No. 20060079569 discloses oral liquid composition consisting duloxetine or pharmaceutically acceptable derivatives thereof.

U.S. Patent Application No. 20070004795 discloses pharmaceutical composition comprising duloxetine or its pharmaceutically acceptable salts thereof and stabilizing amount of at least one buffering agent.

US Application No. 20060182796 discloses taste masked oral pharmaceutical composition containing a pharmaceutically active ingredient coated with a combination an enteric polymer and an ammonio methacrylate copolymer.

U.S. Application No. 20070149479 discloses nanoparticulate inclusion and charge complex, that comprises at least two complex partners, whereby a complex partner is an anionic inclusion-forming agent and another complex partner is a cationic active ingredient.

International (PCT) Application Publication No. WO2007034503A2 discloses controlled release dosage form of duloxetine comprising duloxetine or its pharmaceutically acceptable salts, pharmaceutically acceptable polymeric carrier and solubility enhancer.

International (PCT) Application Publication No. WO2009084017A2 discloses taste masked orally disintegrating tablet composition of memantine in combination with other active agents.

Duloxetine or pharmaceutically acceptable salts thereof are acid labile and degrade in acidic environment of gastrointestinal tract (GIT). Acid hydrolysis of its ether linkage results in 1-naphthol, which is known to be toxic and cause several side effects. Therefore, duloxetine or pharmaceutically acceptable salts thereof need protection from degradation in acidic environment of GIT. Such acid sensitive compounds have been formulated with enteric-coatings to protect them from degradation in stomach. The enteric-coated compositions of duloxetine or pharmaceutically acceptable salts thereof release the drug in lower part of GIT where pH is towards alkaline side. But such compositions result in a lag period from the time of administration of composition to the onset of therapeutic action.

Duloxetine or pharmaceutically acceptable salts thereof have low aqueous solubility and are slightly soluble in water. The low solubility results in practical difficulties in formulating such drugs for oral administration, particularly where early onset of therapeutic effect is desired or required.

Further, duloxetine or pharmaceutically acceptable salts thereof have pungent and bitter taste. In order to improve the acceptability and patient compliance it becomes necessary to mask the taste of such compounds. Thus, there is need to develop a taste masked pharmaceutical composition comprising duloxetine or pharmaceutically acceptable salts thereof having early onset of action with improved solubility.

SUMMARY OF THE INVENTION

In one general aspect there is provided a taste masked pharmaceutical composition of duloxetine or pharmaceutically acceptable salts thereof comprising duloxetine optionally with one or more pharmaceutically acceptable excipients.

Embodiments of the pharmaceutical composition may include one or more of the following features. The taste masking of the pharmaceutical composition is achieved by using one or more of ion exchange resin, methacrylate polymers or cyclodextrin or derivative thereof. The pharmaceutical composition may further include one or more of alkalizer and pharmaceutically acceptable excipients.

In another general aspect there is provided an inclusion complex of duloxetine or pharmaceutically acceptable salts thereof with one or more cyclodextrin or derivatives thereof.

Embodiments of the inclusion complex comprise a pharmaceutical composition comprising the inclusion complex of duloxetine or pharmaceutically acceptable salts thereof with one or more cyclodextrin or derivatives thereof. The pharmaceutical composition comprising may include one or more of the following features. The pharmaceutical composition may further include one or more of alkalizer and pharmaceutically acceptable excipients. The pharmaceutically acceptable excipients may include one or more of fillers, binders, lubricants, glidants, and disintegrants.

In another general aspect there is provided a quick release pharmaceutical composition comprising duloxetine or pharmaceutically acceptable salt thereof optionally with one or more pharmaceutically acceptable excipients, wherein the composition releases not less than about 75% of the dose in 30 min when the composition is tested for dissolution using United States Pharmacopoeia Apparatus 2, paddles@ 50 rpm in 900 mL of 0.1M phosphate buffer, pH 6.8 or acetate buffer pH 4.5.

Embodiments of the pharmaceutical composition may include one or more of the following features. The pharmaceutical composition may further include one or more of alkalizer and pharmaceutically acceptable excipients. The pharmaceutically acceptable excipients may include one or more of fillers, binders, lubricants, glidants, and disintegrants.

The details of one or more embodiments of the inventions are set forth in the description below. Other features, objects and advantages of the inventions will be apparent from the description and claims.

DESCRIPTION OF DRAWINGS

FIG. 1: Dissolution profile of duloxetine suspension

DETAILED DESCRIPTION OF THE INVENTION

The inventors have now developed a taste masked pharmaceutical composition of duloxetine or pharmaceutically acceptable salts thereof, which provides quick onset of action and ease of administration over the marketed formulations. It was observed that when duloxetine is present along with one or more cyclodextrin or derivatives thereof, either as physical admixture or in form of complex or any other physical or chemical association, it results in significant increase in solubility of duloxetine. This may result in increased bioavailability. Further, the composition comprises alkalizer, which is being capable of stabilizing the composition by imparting alkaline pH and preventing degradation of drug in GIT.

In one of the embodiments of the present invention, taste masking of duloxetine is achieved by using one or more ion exchange resin, methacrylate polymers or cyclodextrins or derivatives thereof.

The term "Ion exchange resins" as used herein refers to highly ionic, covalently cross-linked, insoluble polyelectrolytes.

Ion exchange resins are commonly prepared from the styrene and various levels of the cross-linking agent divinyl benzene. When the resin is immersed in a medium in which it is insoluble, the counter ions are mobile and can be exchanged for the other counter ions from the surrounding medium and thus form the complex.

The ion exchange resins comprise cation exchange resins or anion exchange resins comprising one or more of polacrilex resin, polacrilin potassium, sodium polystyrene sulfonated, and cholestyramine resin.

Taste masking of duloxetine or pharmaceutically acceptable salts thereof can be achieved by complexing with it various ion exchange resins of different grades in different ratios. The duloxetine-ion-exchange resin complex can be formulated in granules or powder, which can be further reconstituted to get desired composition.

The unpleasant taste of duloxetine can be masked by using one or more methacrylate polymers or by using one or more ion exchange resins.

Methacrylate polymers used for taste masking comprise one or more of Eudragit EPO or Eudragit E 100.

Taste masking of duloxetine or pharmaceutically acceptable salts thereof can be achieved by admixing or complexing it with one or more of cyclodextrins or derivatives thereof.

Duloxetine-cyclodextrin complex also helps to improve aqueous solubility of the duloxetine. The interior of the cyclodextrin molecule is hydrophobic while the exterior is sufficiently hydrophilic to allow the cyclodextrin to be dissolved in water. This difference between the interior and exterior faces allows the cyclodextrin to act as a host molecule and to form inclusion complexes with duloxetine. The cyclodextrin-duloxetine inclusion complex can then be dissolved in water thereby providing for the introduction of duloxetine that has little or slight aqueous solubility into an aqueous environment.

In one of the embodiments of the invention there is provided a pharmaceutical composition comprising an inclusion complex of duloxetine or pharmaceutically acceptable salts thereof with one or more cyclodextrins or derivatives thereof.

In one of the embodiments, there is provided an admixture of duloxetine or pharmaceutically acceptable salts thereof with one or more of cyclodextrins or derivatives thereof.

In another embodiment of the invention there is provided a pharmaceutical composition comprising an admixture of duloxetine or pharmaceutically acceptable salts thereof with one or more of cyclodextrins or derivatives thereof.

The term "admixture" refers to a state produced by a process comprising mixing duloxetine or salts thereof with cyclodextrin or derivatives thereof.

Cyclodextrins are cyclic oligosaccharides of a-D-glucopyranose containing a relatively hydrophobic central cavity and hydrophilic outer surface. Cyclodextrins, also called "Schardingers dextrins", cycloamyloses, cyclomaltoses and cycloglucans, are oligomers of anhydroglucose, bonded together by alpha 1,4 bonds to form a ringed compound. A six membered ring is called alpha cyclodextrin; seven, beta cyclodextrin, and eight, gamma cyclodextrin. These six, seven and eight membered rings are also referred to as cyclomaltohexaose, cyclomaltoheptaose and cyclomaltoctaose, respectively.

Cyclodextrins and their derivatives are a class of substances that is successfully used for oral or parenteral formulation of poorly soluble pharmaceutical substances. The interior of the cyclodextrin molecule is hydrophobic while the exterior is sufficiently hydrophilic to allow the cyclodextrin to be dissolved in water. This difference between the interior and exterior faces allows the cyclodextrin to act as a host molecule and to form inclusion complexes with poorly soluble pharmaceutical substances. By the formation of an inclusion complex in the hydrophobic interior space of the cyclodextrin, an increased solubility of poorly water-soluble pharmaceutical substances is achieved. This in turn results in a faster rate of solution and can contribute to an increase in bioavailability.

In the pharmaceutical industry, cyclodextrins or derivatives thereof have mainly been used as complexing agents to increase the aqueous solubility of poorly water-soluble drugs, and to increase their bioavailability and stability. Light, thermal and oxidative stability of actives may be improved through the formation of cyclodextrin complexes. In addition, cyclodextrins or derivatives thereof are used to reduce or prevent gastrointestinal or ocular irritation, reduce or eliminate unpleasant smells or tastes, prevent drug-drug or drug-additive interactions, or even to convert oils and liquid drugs into microcrystalline or amorphous powders. Incorporation of cyclodextrin in the composition also prevents discoloration of the dosage form.

Suitable cyclodextrin or derivatives thereof may be selected from α-cyclodextrin, β-cyclodextrin, γ-cyclodextrin, hydroxypropyl-α-cyclodextrin, hydroxypropyl-β-cyclodextrin, dimethyl β-cyclodextrin, 2-hydroxyethyl β-cyclodextrin, trimethyl-β-cyclodextrin, and sulfonated cyclodextrins, in anhydrous or hydrated form.

Hydroxypropyl-β-cyclodextrin, a chemically modified β-cyclodextrin is highly water soluble, stable and its safety and tolerance has been well documented. Its ability to improve aqueous solubility has been attributed to the formation of inclusion complex between cyclodextrins and 'guest' drug molecule. The prepared HP-β-CD complex is stable and reduces oxidation of duloxetine in the dosage form, which further increases dissolution rate of the formulation. Incorporation of cyclodextrin in the composition also prevents discoloration of the dosage form.

The composition of the present invention can be formulated by preparing inclusion complex and/or by preparing admixture or any other physical or chemical association of duloxetine or pharmaceutically acceptable salts thereof with one or more cyclodextrin or derivative thereof by the various processes known in the art and optionally blending this complex with suitable excipients and converting into suitable dosage form.

In one of the embodiments of the present invention, the quick release composition is taste masked by using one or more of ion exchange resin, methacrylate polymers or cyclodextrin or derivative thereof.

The pharmaceutical composition of the present invention can be present in the form of tablet, capsule, powder, disc, caplet, granules, pellets, granules in capsule, minitablets, minitablets in capsule, pellets in capsule, sachet, orally disintegrating tablet, chewable tablet, effervescent tablet, mouth dissolving film, syrup, solution, suspension, elixir, emulsion and other dosage forms suitable for oral administration.

The tablet may vary in shapes such as oval, round, triangle, almond, peanut, pentagonal, trapezoidal, and parallelogram.

The granules can be prepared by wet granulation, dry granulation method.

In one of the embodiments of the present invention, the taste masked pharmaceutical composition is in the form of powder for suspension.

In one of the embodiments of the present invention, the quick release composition is in form of powder for suspension.

In one of the embodiments of present invention, an oral suspension is prepared by mixing a powder for oral suspension, with a suitable aqueous vehicle. A powder for oral suspension comprises at least one alkalizer and optionally other pharmaceutically acceptable excipients.

The pharmaceutical composition of the invention further comprises one or more pharmaceutically acceptable alkalizer, said alkalizer being capable of stabilizing the composition by imparting alkaline pH to surrounding environment of individual duloxetine particle. The amount of alkalizer present in the composition is sufficient to increase the gastric fluid pH of the stomach to a pH that prevents or inhibits acid degradation of the duloxetine or pharmaceutically acceptable salts thereof in the gastric fluid of the stomach.

The composition comprises the drug substance and an alkalizer, said alkalizer being capable of stabilizing the composition by imparting alkaline pH to surrounding environment of individual duloxetine particle.

In an another embodiment, the composition comprises the drug substance and an alkalizer, said alkalizer being capable of stabilizing the composition by imparting alkaline pH to an aqueous solution or dispersion of the composition when reconstituted with suitable vehicle.

The amount of alkalizer present in the composition is sufficient to increase the gastric fluid pH of the stomach to a pH that prevents or inhibits acid degradation of the duloxetine or pharmaceutically acceptable salts thereof in the gastric fluid of the stomach.

The alkalizer is used in an amount sufficient to substantially achieve the above functionality. Many weak and strong bases (and mixtures thereof) can be utilized as alkalizers. Therefore, the alkalizers of the present invention elevate the pH of the stomach sufficiently to achieve adequate bioavailability of the drug to effect therapeutic action.

Alkalizers may be selected from one or more agents selected from alkalizer may be selected from one or more of a salt of a Group IA metal, an alkali earth metal buffering agent, a calcium buffering agent, a magnesium buffering agent, and an aluminum buffering, sodium bicarbonate, potassium bicarbonate, magnesium hydroxide, magnesium lactate, magnesium gluconate, magnesium oxide, magnesium aluminate, magnesium carbonate, magnesium silicate, magnesium citrate, aluminum hydroxide, aluminum phosphate, aluminum hydroxide/magnesium carbonate, potassium carbonate, potassium citrate, aluminum hydroxide/sodium bicarbonate coprecipitate, aluminum glycinate, aluminum magnesium hydroxide, sodium citrate, sodium tartrate, sodium acetate, sodium carbonate, sodium (polyphosphate, sodium dihydrogen phosphate, potassium polyphosphate, sodium pyrophosphate, potassium pyrophosphate, disodium hydrogenphosphate, dipotassium hydrogenphosphate, trisodium phosphate, tripotassium phosphate, potassium metaphosphate, calcium acetate, calcium glycerophosphate, calcium chloride, calcium hydroxide, calcium lactate, calcium carbonate, calcium gluconate, calcium bicarbonate, calcium citrate, calcium phosphate magnesium phosphate, potassium phosphate, sodium phosphate, trihydroxymethylaminomethane, ail amino acid, an acid salt of an amino acid, an alkali salt of an amino acid, and combinations of any of the foregoing.

The pharmaceutical composition of the invention further may comprise pharmaceutically acceptable excipients wherein excipients may be selected from one or more of binders, fillers, disintegrants, glidants, lubricants, surfactants, thickening agent, sweeteners and flavors.

Suitable binder may include one or more of, povidone, starch, stearic acid, gums, celluloses, alginic acids, chitosan, chitin, or polyethylene glycol.

Suitable fillers may include one or more of saccharose, glucose, fructose, maltose, maltitol, mannitol, dextrins such as maltodextrins; xylitol, sorbitol, microcrystalline cellulose, titanium dioxide, calcium phosphate, calcium sulfate, kaolin, dry starch, powdered sugar, or silicates such as magnesium aluminium silicate.

Suitable disintegrant may include one or more of starch, croscarmellose sodium, crospovidone, pregelatinized starch or sodium starch glycolate.

Suitable glidant may include one or more of colloidal silicon dioxide, talc or cornstarch.

Suitable lubricant may include one or more of magnesium stearate, zinc stearate, calcium stearate, stearic acid, sodium stearyl fumarate, hydrogenated vegetable oil, or glyceryl behenate.

Suitable surfactants are those known to ordinary skilled in the art and may include but not limited to amphoteric, non-ionic, cationic or anionic surfactants. Suitable surfactants comprises one or more of sodium lauryl sulfate, monooleate, monolaurate, monopalmitate, monostearate or another ester of polyoxyethylene sorbitane, sodium dioctylsulfosuccinate (DOSS), lecithin, stearylic alcohol, cetostearylic alcohol, cholesterol, polyoxyethylene ricin oil, polyoxyethylene fatty acid glycerides, poloxamer, or cremophore RH 40.

Suitable thickening agent may include one or more of methylcellulose, carboxymethylcellulose, microcrystalline cellulose, ethylcellulose, hydroxyethylcellulose, hydroxypropylcellulose, hydroxypropylmethylcellulose, alginate, carageenan, xanthan gum, acacia, tragacanth, locust bean gum, guar gum, carboxypolymethylene, polyvinyl pyrrolidone, polyvinyl alcohol, poloxamer, magnesium aluminum silicate (veegum), bentonite, hectorite, povidone, and maltol, or combination thereof.

Suitable sweetener may include one or more of monosaccharides, disaccharides and polysaccharides, e.g. xylose, ribose, glucose, mannose, galactose, fructose, sucrose, maltose, invert sugar, partially hydrolyzed starch, corn syrup solids, mannitol, xylitol, D-sorbitol, erythritol, pentitol, hexitol, malitol, dihydrochalcones, monellin, steviosides or glycyrrhizin; saccharin in free acid form, soluble saccharin salts, e.g. sodium or calcium saccharin salts, cyclamate salts or acesulfame K; dipeptide based sweeteners, such as L-aspartic acid derived sweeteners, e.g. aspartame; water-soluble sweeteners derived from naturally occurring water-soluble sweeteners, e.g. sucralose; or protein based sweeteners, e.g. thaumatococcus danielli (Thaumatin I and II).

Suitable flavoring agents may include those known to the skilled artisan, such as natural, "natural-like" and artificial flavors. These flavors may be chosen e.g. from synthetic flavor oils, flavoring aromatics, oleo-resins and extracts derived e.g. from plants, leaves, flowers or fruits.

Representative flavors may include one or more of spearmint oil, cinnamon oil, peppermint oil, clove oil, bay oil, thyme oil, cedar leaf oil, oil of nutmeg, oil of sage, oil of bitter almonds, vanilla, chocolate, coffee, cocoa and citrus oil, lemon, orange, cherry, grape, lime or grapefruit, and fruit essences, e.g. apple, pear, peach, strawberry, raspberry, cherry, plum, pineapple or apricot; mints such as peppermint (including menthol, especially levomenthol), aldehydes and esters, e.g. cinnamyl acetate, cinnamaldehyde, citral, diethylacetal, dihydrocarvyl acetate, eugenyl formate or p-methylanisol; alpha-citral (geranial) and beta-citral (neral); decanal; ethyl vanillin; piperonal (heliotropine); vanillin; alpha-amyl cinnamaldehyde; butyraldehyde; valeraldehyde; citronellal; decanal; aldehyde C-8; aldehyde C-9; aldehyde C-12; 2-ethyl butyraldehyde; hexenal, i.e. trans-2; tolyl aldehyde; veratraldehyde; 2,6-dimethyl-5-heptenal (melonal); 2-6-dimethyloctanal; or 2-dodecenal.

Moreover, the composition of the invention optionally include usual auxiliaries known in the art such as saliva stimulating agents like citric acid, lactic acid, malic acid, succinic acid, ascorbic acid, adipic acid, fumaric acid, tartaric acids; cooling sensation agents like maltitol, monomenthyl succinate, ultracool; stabilizers like gums, agar; taste masking agents like acrylic polymers, copolymers of acrylates, celluloses, resins; coloring agents like titanium dioxide, natural food colors, dyes suitable for food, drug and cosmetic applications; preservatives like alpha-tocopherol, citric acid, butylated hydroxytoluene, butylated hydroxyanisole, ascorbic acid, fumaric acid, malic acid, sodium ascorbate or ascorbic acid palmitate or effervescing agents like citric acid, tartaric acid, sodium bicarbonate, or sodium carbonate.

The pharmaceutical composition of the present invention can be formulated by the various processes known in the art. The manufacturing processes may employ one or a combination of established methods comprising dry mixing; milling; grinding, sifting, sieving, dry granulation, wet granulation. The composition of the invention is prepared by dissolving duloxetine in taste masking agent in a suitable vehicle. Further colloidal silicon dioxide and other suitable excipients are added to form uniform dispersion. The dispersion is dried at 5° C. for 24 hours. The dried material is passed through suitable mesh and further converted into suitable dosage form.

The composition of the invention is prepared by granulating duloxetine along with one or more taste-masking excipients in a suitable vehicle. The taste-masked granules so obtained are mixed with suitable flavors, thickening agents, sweetners and other suitable excipients. The resultant powder blend is dispensed in HDPE bottles for reconstitution with water at the time of use.

Dissolution studies are performed using United States Pharmacopoeia Apparatus 2, paddles@ 50 rpm in 900 mL of 0.1M phosphate buffer, pH6.8 and acetate buffer pH 4.5 to ascertain the percentage dissolved.

While the present invention has been described in terms of its specific embodiments, certain modifications and equivalents will be apparent to those skilled in the art and are intended to be included within the scope of the present invention.

The invention is further illustrated by the following examples which are provided merely to be exemplary of the invention and do not limit the scope of the invention. Certain modifications and equivalents will be apparent to those skilled in the art and are intended to be included within the scope of the invention.

EXAMPLE 1

Duloxetine Composition

TABLE 1

Complex of Duloxetine and taste masking agent

| Ingredient | % w/w |
|---|---|
| Duloxetine hydrochloride | 10-30 |
| Eq. to Duloxetine 60 mg | |
| Eudragit EPO | 30-70 |
| Colloidal Silicon Dioxide | 20-40 |
| Alcohol | Lost in processing |
| Purified Water | Lost in processing |
| Total weight | 100% |

Procedure for complexation: Duloxetine hydrochloride and Eudragit EPO are dissolved in alcohol with stirring to form clear solution. Purified water is added to above solution with stirring. Further colloidal silicon dioxide is added to form uniform dispersion. The dispersion is dried at 50° C. for 24 hours. The dried material is passed through 100 mesh.

TABLE 2

Composition of powder for oral suspension:

| Ingredient | % w/w |
|---|---|
| Duloxetine hydrochloride/ Eudragit EPO complex | 5-25 |
| Sugar | 15-35 |
| Magnesium Oxide | 15-40 |
| Microcrystalline Cellulose/ Sodium Carboxymethyl Cellulose | 10-25 |
| Sodium Carboxymethyl Cellulose | 2-10 |
| Sodium Chloride | 0-2 |
| Sodium Lauryl Sulphate | 0-2 |
| Poloxamer 188 | 0-5 |
| Sucralose | 0-2 |
| Peppermint Powder Flavour | 0-8 |
| Colloidal Silicon Dioxide | 0-5 |
| Vanilla Cream Powder Flavour | 0-5 |

Procedure for power for suspension: Weighed amount of sugar, magnesium oxide, microcrystalline cellulose, sodium carboxymethyl cellulose are co-sifted through 60 mesh and mixed well. Weighed amount of sodium chloride, sodium lauryl sulphate, Poloxamer 188, and sucralose are cosifted through 60 mesh and mixed with the above bulk. Peppermint powder flavour & Vanilla cream powder flavour are cosifted through 80 mesh and mixed with above bulk. To the bulk duloxetine hydrochloride/Eudragit EPO complex was added followed by addition of colloidal silica. The blend was mixed well. The equivalent six doses of powder blend of duloxetine were filled in each amber colored glass bottle.

EXAMPLE 2

Duloxetine Composition for Powder for Suspension

TABLE 3

Composition of powder for oral suspension:

| S. No. | Ingredient | % w/w |
|---|---|---|
| | Intragranular-I | |
| 1. | Duloxetine HCl | 1.51 |
| 2. | Eudragit EPO | 3-6 |
| 3. | Hydroxypropylmethylcellulose E6 LV | 0.5-2 |
| 4. | Mannitol 25 | 40-60 |
| 5. | Talc | 3-5 |
| | Intragranular-II | |
| 6. | Light Magnesium Oxide | 10-12 |
| 7. | Sugar (60-200#) | 8-11 |
| 8. | HPMC E6 LV | 0.1-0.3 |
| | Extragranular-I | |
| 9. | Avicel RC 591 (MCC + Na CMC) | 5-8 |
| 10. | Hydroxy Ethyl Cellulose | 1-2 |
| 11. | Sodium Chloride | 0.1-1 |
| 12. | Poloxamer 188 | 4-6 |
| 13. | Sucralose | 0.1-1 |
| 14. | Banana flavor | 1-2 |
| 15. | Talc | 0.1-0.3 |
| | Extragranular-II | |
| 16. | Sugar (60-200#) | 2-5 |
| | Total wt/dose | 100.00 |

Procedure for Intragranular-I: Duloxetine hydrochloride was dissolved in 1:1 mixture of isopropyl alcohol and dichloromethane. Weighed amount of Eudragit EPO was added to the above solution with stirring till clear solution was obtained. Hydroxypropylmethylcellulose E6, Mannitol 25 and Talc were mixed, co-sieved through 40# and then granulated with the solution containing duloxetine and Eudragit EPO in rapid mixer granulator. The wet mass so obtained was dried and milled to obtain 60# pass granules.

Procedure for Intragranular-II: Light magnesium oxide and sugar were mixed and granulated in rapid mixer granulator using Hydroxypropylmethylcellulose E6 dissolved in 1:1 mixture of isopropyl alcohol and dichloromethane. The wet mass so obtained was dried and milled to obtain 40# pass granules.

Procedure for Extragranular-I: Avicel RC-591 (MCC/CMC Sodium), Hydroxyethyl cellulose (Natrosol 250M Pharm), Sodium Chloride, Poloxamer 188, Sucralose, Banana flavor & Talc were weighed in requisite quantities and cosifted.

Procedure for Extragranular-II: Requisite quantity of sugar was weighed and sieved.

Final Blending: Intragranular I, Intragranular II, Extragranular-I and Extragranular-II portions were mixed in double cone blender. The equivalent eight doses of powder blend of duloxetine were filled in each high density polyethylene bottles.

EXAMPLE 3

Dissolution Studies

The powder for suspension, exemplified in Example 2, contained in one bottle was reconstituted using 98 ml of water. Dissolution studies were performed using the 15 ml of reconstituted suspension (equivalent to 60 mg of duloxetine) in United States Pharmacopoeia Apparatus 2, paddles@ 50 rpm in 900 mL of 0.1M phosphate buffer, pH6.8 and acetate buffer pH 4.5 to ascertain the percentage dissolved. Samples from the dissolution apparatus were withdrawn at 15 min, 30 min, 45 min, 60 min and 90 min and were analyzed for drug content using standard techniques. FIG. 1 illustrates the dissolution profile of the reconstituted suspension containing duloxetine.

EXAMPLE 4

Duloxetine Sachet

TABLE 4

Duloxetine Sachet

| Sr. No. | Ingredients | (% w/w) |
|---|---|---|
| 1 | Duloxetine Hydrochloride | 5-20 |
| 2 | Hydroxypropyl-beta-cyclodextrin | 0-50 |
| | Extragranular | |
| 3 | Mannitol | 5-30 |
| 4 | Sodium bicarbonate | 10-95 |
| 5 | Sucralose | 1-10 |
| 6 | Mint flavor | 1-10 |
| 7 | Taste masking flavour | 1-10 |
| 8 | Xanthan gum | 0.5-10 |

Procedure:

Weighed amount of Hydroxypropyl-Beta-Cyclodextrin was dissolved in required quantity of water. Weighed amount of duloxetine hydrochloride was added to above solution and stirred for a period of 10-15 minutes. The solution was freeze-dried to get the dried complex. The dried complex was sifted through 30 mesh followed by 60 mesh. Weighed required quantity of Mannitol, sodium bicarbonate were sifted through 40 mesh and mixed with the complex. Weighed required quantity of sucralose, mint flavour, taste masking flavour, and xanthan gum were sifted through 60 mesh and added to the above blend followed by mixing. The blend was filled as per the sachet weight and sealed.

EXAMPLE 5

Solubility Studies

Weighed amount of duloxetine hydrochloride was dispersed in required quantity of water at room temperature. To the above dispersion sodium bicarbonate, propylene glycol, sodium lauryl sulphate or Hydroxypropyl Beta-cyclodextrin was added in requisite amount as specified in Table 5. The resultant solution was observed for turbidity or clarity.

TABLE 5

Solubility Studies

| S. No. | Duloxetine HCl | PG | SLS | HP-βCD | Sodium Bicarbonate | Water | Observation |
|---|---|---|---|---|---|---|---|
| 1 | 20 mg | — | — | — | 1.6 g | 125 ml | Turbid solution* |
| 2 | 20 mg | — | — | — | 1.75 g | 125 ml | Turbid solution* |
| 3 | 20 mg | 2 g | — | — | 1.75 g | 125 ml | Turbid solution* |
| 4 | 20 mg | — | 5 mg | — | 1.75 g | 125 ml | Turbid solution* |
| 5 | 20 mg** | — | — | 99.0 mg | 1.75 g | 125 ml | Clear solution |

20 mg of Duloxetine is equivalent to 22.4 mg of Duloxetine HCl
SLS - Sodium Lauryl Sulphate
PG - Propylene glycol
HP-βCD - Hydroxy propyl Beta-cyclodextrin
*Duloxetine was precipitate out and stick to the wall of the container and formed a film
**Duloxetine was complexed with HP-βCD

EXAMPLE 6

Sensory Evaluation

Ten panelist evaluated the taste masking of the composition specified in example 4 on sensory evaluation criteria of score 1 to 9 for different attributes such as Flavor, consistency, mouth feel and taste, where score 1 meant disliked extremely and score 9 meant liked extremely. The results are enumerated in Table 6.

TABLE 6

Sensory Evaluation

| Panelist | Attributes Evaluated | | | |
|---|---|---|---|---|
| | Flavor | Consistency | Mouth feel | Taste |
| 1 | 7 | 5 | 7 | 8 |
| 2 | 7 | 9 | 4 | 5 |
| 3 | 7 | 9 | 7 | 7 |
| 4 | 5 | 7 | 7 | 6 |
| 5 | 9 | 8 | 8 | 7 |
| 6 | 5 | 8 | 8 | 5 |
| 7 | 6 | 7 | 6 | 4 |
| 8 | 5 | 7 | 4 | 4 |
| 9 | 6 | 9 | 7 | 8 |
| 10 | 7 | 7 | 6 | 7 |
| Average Scores | 6.40 | 7.60 | 6.40 | 6.10 |

Sensory Evaluation Criteria

| Score | Observation |
|---|---|
| 9 | Liked extremely |
| 8 | Liked very much |
| 7 | Liked moderately |
| 6 | Liked slightly |
| 5 | Neither liked nor disliked |
| 4 | Disliked slightly |
| 3 | Disliked moderately |
| 2 | Disliked very much |
| 1 | Disliked extremely |

While the invention has been described in terms of its specific embodiments, certain modifications and equivalents will be apparent to those skilled in the art and are intended to be included within the scope of the invention.

We claim:

1. A taste masked pharmaceutical composition of duloxetine or pharmaceutically acceptable salts thereof consisting of duloxetine or pharmaceutically acceptable salts thereof and one or more ion exchange resin or methacrylate polymer; wherein the pharmaceutical composition further comprises cyclodextrin or a derivative thereof; wherein the pharmaceutical composition is taste masked.

2. The taste masked pharmaceutical composition according to claim 1, wherein the ion exchange resin is one or more of cation exchange resins or an anion exchange resins.

3. The taste masked pharmaceutical composition as according to claim 2, wherein the ion exchange resin is one or more of polacrilex resin, polacrilin potassium, sodium polystyrene sulfonated, and cholestyramine resin.

4. The taste masked pharmaceutical composition according to claim 1, wherein composition comprises an inclusion complex of duloxetine or pharmaceutically acceptable salt with cyclodextrin or derivative thereof.

5. The taste masked pharmaceutical composition according to claim 1, wherein pharmaceutical composition comprises an admixture of duloxetine or pharmaceutically acceptable salt with cyclodextrin or derivative thereof.

6. The taste masked pharmaceutical composition according to claim 1, wherein cyclodextrin or derivatives thereof are selected from the group consisting of α-cyclodextrin, β-cyclodextrin, γ-cyclodextrin, hydroxypropyl-α-cyclodextrin, hydroxypropyl-β-cyclodextrin, dimethyl-β-cyclodextrin, 2-hydroxyethyl βcyclodextrin, trimethyl-β-cyclodextrin, and sulfonated cyclodextrins, in anhydrous or hydrated form.

7. The taste masked pharmaceutical composition according to claim 1, wherein the pharmaceutical composition is in the form of a tablet, capsule, powder, disc, caplet, granules, pellets, granules in capsule, minitablets, minitablets in capsule, pellets in capsule, sachet, orally disintegrating tablet, chewable tablet, effervescent tablet, mouth dissolving film, syrup, solution, suspension, powder for suspension, elixir, emulsion and other dosage forms suitable for oral administration.

8. The taste masked pharmaceutical composition according to claim 7, wherein the pharmaceutical composition is in the form of powder for suspension.

9. A pharmaceutical composition consisting of:

| Ingredient | % w/w |
|---|---|
| Duloxetine hydrochloride Eq. to Duloxetine 60 mg | 10-30 |
| Eudragit EPO | 30-70 |
| Colloidal Silicon Dioxide | 20-40 |
| Alcohol | Lost in processing |

-continued

| Ingredient | % w/w |
|---|---|
| Purified Water | Lost in processing |
| Total weight | 100%. |

10. A pharmaceutical composition comprising:

| Ingredient | % w/w |
|---|---|
| Duloxetine hydrochloride/Eudragit EPO complex | 5-25 |
| Sugar | 15-35 |
| Magnesium Oxide | 15-40 |
| Microcrystalline Cellulose/Sodium Carboxymethyl Cellulose | 10-25 |
| Sodium Carboxymethyl Cellulose | 2-10 |
| Sodium Chloride | 0-2 |
| Sodium Lauryl Sulphate | 0-2 |
| Poloxamer 188 | 0-5 |
| Sucralose | 0-2 |
| Peppermint Powder Flavour | 0-8 |
| Colloidal Silicon Dioxide | 0-5 |
| Vanilla Cream Powder Flavour | 0-5. |

11. A pharmaceutical composition comprising:

| Ingredient | % w/w |
|---|---|
| Duloxetine hydrochloride/Eudragit EPO complex | 5-25 |
| Sugar | 15-35 |
| Magnesium Oxide | 15-40 |
| Microcrystalline Cellulose/Sodium Carboxymethyl Cellulose | 10-25 |
| Sodium Carboxymethyl Cellulose | 2-10 |
| Sodium Chloride | 0-2 |
| Sodium Lauryl Sulphate | 0-2 |
| Poloxamer 188 | 0-5 |
| Sucralose | 0-2 |
| Peppermint Powder Flavour | 0-8 |
| Colloidal Silicon Dioxide | 0-5 |
| Vanilla Cream Powder Flavour | 0-5. |

12. A pharmaceutical composition comprising:

| S. No. | Ingredient | % w/w |
|---|---|---|
| Intragranular-I | | |
| 1 | Duloxetine HCl | 1.51 |
| 2. | Eudragit EPO | 3-6 |
| 3. | Hydroxypropylmethylcellulose E6 LV | 0.5-2 |
| 4. | Mannitol 25 | 40-60 |
| 5. | Talc | 3-5 |
| Intragranular-II | | |
| 6. | Light Magnesium Oxide | 10-12 |
| 7. | Sugar (60-200#) | 8-11 |
| 8. | HPMC E6 LV | 0.1-0.3 |
| Extragranular-I | | |
| 9. | Avicel RC 591 (MCC + Na CMC) | 5-8 |
| 10. | Hydroxy Ethyl Cellulose | 1-2 |
| 11. | Sodium Chloride | 0.1-1 |
| 12. | Poloxamer 188 | 4-6 |
| 13. | Sucralose | 0.1-1 |
| 14. | Banana flavor | 1-2 |
| 15. | Talc | 0.1-0.3 |
| Extragranular-II | | |
| 16. | Sugar (60-200#) | 2-5 |
| | Total wt/dose | 100.00. |

13. Duloxetine Sachet comprising:

| Sr. No. | Ingredients | (% w/w) |
|---|---|---|
| 1 | Duloxetine Hydrochloride | 5-20 |
| 2 | Hydroxypropyl-beta-cyclodextrin | 0-50 |
| Extragranular | | |
| 3 | Mannitol | 5-30 |
| 4 | Sodium bicarbonate | 10-95 |
| 5 | Sucralose | 1-10 |
| 6 | Mint flavor | 1-10 |
| 7 | Taste masking flavour | 1-10 |
| 8 | Xanthan gum | 0.5-10. |

* * * * *